(12) United States Patent
Sung

(10) Patent No.: US 8,481,007 B2
(45) Date of Patent: *Jul. 9, 2013

(54) COMPOSITIONS AND METHODS FOR PROVIDING ULTRAVIOLET RADIATION PROTECTION

(76) Inventor: Chien-Min Sung, Tansui (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/071,050

(22) Filed: Mar. 24, 2011

(65) Prior Publication Data

US 2011/0286943 A1    Nov. 24, 2011

Related U.S. Application Data

(63) Continuation-in-part of application No. 11/640,136, filed on Dec. 14, 2006, which is a continuation-in-part of application No. 10/814,660, filed on Mar. 30, 2004, now Pat. No. 7,294,340.

(60) Provisional application No. 61/317,135, filed on Mar. 24, 2010, provisional application No. 61/354,109, filed on Jun. 11, 2010.

(51) Int. Cl.
*A61Q 17/04*    (2006.01)
*A61K 8/00*    (2006.01)

(52) U.S. Cl.
USPC ........................................... 424/59; 427/401

(58) Field of Classification Search
USPC .................................. 424/59, 401
See application file for complete search history.

(56) References Cited

U.S. PATENT DOCUMENTS

| | | | |
|---|---|---|---|
| 3,944,506 A | 3/1976 | Hramchenko et al. | |
| 4,048,123 A | 9/1977 | Hramchenko et al. | |
| 4,414,199 A | 11/1983 | Strobridge | |
| 4,482,538 A | 11/1984 | Davies | |
| 4,737,307 A | 4/1988 | Brown et al. | |
| 5,326,483 A | 7/1994 | Halloran et al. | |
| 5,616,331 A * | 4/1997 | Allard et al. ................. | 424/401 |
| 5,709,577 A | 1/1998 | Jin et al. | |
| 5,725,866 A | 3/1998 | Ramin | |
| 5,882,636 A | 3/1999 | Mui et al. | |
| 5,968,490 A | 10/1999 | Sun et al. | |
| 5,985,300 A | 11/1999 | Crotty et al. | |
| 6,004,539 A | 12/1999 | Longo, Jr. et al. | |
| 6,020,395 A | 2/2000 | Angeletakis | |
| 6,106,818 A | 8/2000 | Dulog et al. | |
| 6,117,415 A | 9/2000 | Schwarz | |
| 6,121,344 A | 9/2000 | Angeletakis et al. | |
| 6,123,925 A | 9/2000 | Barry et al. | |
| 6,156,325 A | 12/2000 | Farer et al. | |
| 6,187,327 B1 | 2/2001 | Stack | |
| 6,207,175 B1 | 3/2001 | Lebreton | |
| 6,232,637 B1 | 5/2001 | Gardner et al. | |
| 6,248,339 B1 | 6/2001 | Knitowski et al. | |
| 6,306,805 B1 | 10/2001 | Bratescu et al. | |
| 6,352,687 B1 | 3/2002 | Ismailer et al. | |
| 6,358,499 B2 | 3/2002 | Hall-Puzio et al. | |
| 6,428,794 B1 | 8/2002 | Klofta et al. | |
| 6,500,183 B1 | 12/2002 | Waldrom | |
| 6,503,488 B1 | 1/2003 | Rosen et al. | |
| 6,518,228 B1 | 2/2003 | Jorgensen et al. | |
| 6,579,516 B1 | 6/2003 | Mansouri | |
| 6,593,395 B2 | 7/2003 | Angeletakis et al. | |
| 6,607,719 B2 | 8/2003 | Uemura et al. | |
| 6,716,451 B1 | 4/2004 | Udell et al. | |
| 6,751,506 B2 | 6/2004 | Shealy | |
| 7,294,340 B2 | 11/2007 | Sung et al. | |
| 7,384,436 B2 | 6/2008 | Sung | |
| 2003/0032693 A1 | 2/2003 | Angeletakis et al. | |
| 2003/0049291 A1 | 3/2003 | Cheski | |
| 2003/0059389 A1 | 3/2003 | Tournilhac et al. | |
| 2003/0064086 A1 | 4/2003 | Carrion et al. | |
| 2003/0165550 A1 | 9/2003 | Rhoades | |
| 2003/0211954 A1 | 11/2003 | Kono et al. | |
| 2005/0158549 A1 | 7/2005 | Khabashesku et al. | |
| 2005/0220829 A1 | 10/2005 | Sung et al. | |
| 2006/0271132 A1 | 11/2006 | Fiset | |
| 2007/0184121 A1 | 8/2007 | Sung | |
| 2008/0219939 A1 | 9/2008 | Grune | |
| 2009/0220556 A1 | 9/2009 | Shenderova et al. | |
| 2009/0224370 A1 | 9/2009 | Slutz | |
| 2009/0226495 A1 | 9/2009 | Picardi et al. | |

FOREIGN PATENT DOCUMENTS

JP          2003081768 A  *  3/2003
WO    WO 2004/039346          5/2004

OTHER PUBLICATIONS

Higuchi, T. et al. "Cosmetic", JP 2003-081768, Mar. 19, 2003, English translation (PTO 11-4481).*
Raty et al; Ultradispersity of Diamond at the Nanoscale; Nature Materials; Dec. 2003; pp. 792-755; vol.2; Nature Publishing Group.
Flick; Cosmetic Additive; 1991; p. 635; Noyes Publications.
Rittner; Nanoparticles—What's Now, What's Next?; Chemical Engineering Process; Nov. 2003; pp. 39s-42s.
Xu et al; A New method for Deaggregation of Nanodiamond from Explosive Detonation: Graphitization-Oxidation Method; Physics of the Solid Stat; 2004; vol. 46, No. 4; 633-634.
Zhu et al; Chemical Mechanical Modification of Nanodiamond in Aqueous System; 2004; pp. 665-667.
U.S. Appl. 11/897,010, filed Aug. 27, 2007; Chien-Min Sung.
U.S. Appl. No. 13/115,328, filed May 25, 2011; Chien-Min Sung.
U.S. Appl. No. 11/640,136, filed Dec. 14, 2006; Chien-Min Sung; office action issued Jul. 20, 2011.
Ansel's Pharmaceutical and dosage Forms and Drug Delivery Systems; 2005(8th Ed. By Loyd Allen, Jr.)Lippincott Williams and Wilkins; pp. 168-172.
Higuchi e tal; Cosmetic Preparation; May 13, 2004; Derwent Acc No. 2004-390197; Abstract.
U.S. Appl. No. 13/115,328, filed May 25, 2011; Chien-Min Sung; office action dated Sep. 10, 2012.
U.S. Appl. No. 11/640,136; filed Dec. 14, 2006; Chien-Min Sung; office action dated Dec. 14, 2012.
U.S. Appl. No. 13/115,328; filed May 25, 2011; Chien-Min Sung; office action dated Mar. 18, 2013.

* cited by examiner

*Primary Examiner* — Gina C Justice
(74) *Attorney, Agent, or Firm* — Thorpe North & Western LLP

(57) ABSTRACT

The present invention provides sunscreen compositions and associated methods. In one aspect, for example, a sunscreen composition can include a cosmetically acceptable carrier and a plurality of nanoparticles dispersed in the carrier with a dispersant. The nanoparticles include at least one sun-block functional group operable to provide UV radiation protection. In one aspect the nanoparticles can be nanodiamond particles.

8 Claims, No Drawings

COMPOSITIONS AND METHODS FOR PROVIDING ULTRAVIOLET RADIATION PROTECTION

PRIORITY DATA

This application claims the benefit of U.S. Provisional Patent Application Ser. No. 61/317,135, filed on Mar. 24, 2010, which is incorporated herein by reference in its entirety. This application is also a continuation-in-part of U.S. patent application Ser. No. 11/640,136, filed on Dec. 14, 2006, which is a continuation-in-part of U.S. patent application Ser. No. 10/814,660, filed Mar. 30, 2004, both of which are hereby incorporated herein by reference. This application also claims the benefit of U.S. Provisional Patent Application Ser. No. 61/354,109, filed on Jun. 11, 2010, which is incorporated herein by reference in its entirety.

FIELD OF THE INVENTION

The present invention relates to compositions and to methods for protecting a subject from ultraviolet radiation. Accordingly, the present invention involves the fields of chemistry and healthcare.

BACKGROUND OF THE INVENTION

Skin cancer is a malignant growth on the skin that can originate from various sources. Three common skin cancers include basal cell cancer, squamous cell cancer, and melanoma. Skin cancer often develops in the epidermis, and is thus often readily detected in early stages. Skin cancer represents the most commonly diagnosed cancer, surpassing lung, breasts, colorectal, and prostate cancer. It has been estimated that approximately 85% of cases of skin cancer are caused by long periods of exposure to ultraviolet (UV) radiation from the sun. Additionally, individuals with lighter skin are more likely to develop skin cancer from such UV exposure.

Sunscreen (or sun-block) is a composition that is applied to a subject's skin in order to absorb or reflects a portion of the sun's UV radiation impinging on the skin that is exposed to sunlight. When used properly and consistently, sunscreen can thus reduce the chances for an individual to develop skin cancer. In addition, sunscreen use can help protect against sunburn. As such, many medical organizations, such as the American Cancer Society, strongly recommend the use of sunscreen as a protection against some forms of skin cancer.

SUMMARY OF THE INVENTION

The present invention provides compositions and methods to provide protection to a subject from harmful ultraviolet (UV) radiation. In one aspect, for example, a remedial healthcare nanodiamond composition can include a cosmetically acceptable carrier and a plurality of nanodiamond particles dispersed in the carrier with a dispersant, where the nanodiamond particles have an average size of from about 0.5 nm to about 50 nm. The composition also includes a sun-block agent. In one aspect, the composition can be formulated as a lotion.

A number of cosmetically acceptable carriers and dispersants are contemplated, and any carrier/dispersant combination capable of forming a dispersion of nanodiamond particles should be seen to be within the present scope. In one aspect, non-limiting examples of carriers can include water, gels, glycerin, alcohols, emollients, fatty acids, fatty alcohols, maltodextrin, carrageenans, MCC, sugars, alcohol sugars, lactose, and combinations thereof. In another aspect, non-limiting examples of dispersants can include anionic surfactants, electrolytes, alcohols, metal chlorides, metal nitrates, viscous biologically acceptable carriers, and combinations thereof.

The nanodiamond particles of the present application can be utilized in various sizes and proportions. In one aspect, for example, the nanodiamond particles have an average size of from about 0.5 nm to about 50 nm. In another aspect the nanodiamond particles have an average size from about 0.5 nm to about 10 nm. In yet another aspect the nanodiamond particles have an average size of less than or equal to about 5 nm. Furthermore, in one aspect the nanodiamond particles comprise from about 1 wt % to about 60 wt % of the composition. In another aspect the nanodiamond particles comprise from about 1 wt % to about 20 wt % of the composition. In yet another aspect the nanodiamond particles comprise less than or equal to about 5 wt % of the composition.

A variety of sun-block agents are contemplated, and any such agent that can provide UV radiation protection to the skin should be considered to be within the present scope. In one aspect, for example, the sun-block agent can include amino, carboxyl, hydroxyl, carbonyl, pyridine, $TiO_2$, $CEO_2$, ZnO, and the like, as well as combinations thereof. In one specific aspect, the sun-block agent is coupled to the nanodiamond particles.

The present invention additionally provides sunscreen compositions. In one aspect such a composition can include a cosmetically acceptable carrier and a plurality of nanoparticles dispersed in the carrier with a dispersant. The nanoparticles include at least one sun-block functional group operable to provide UV radiation protection. In one specific aspect the carrier is a water-based carrier.

Various functional groups are contemplated for providing UV radiation protection. It should be noted that any functional group that can provide UV radiation protection and is capable of being bonded to a nanodiamond particle should be considered to be within the present scope. Non-limiting examples include amino, carboxyl, hydroxyl, carbonyl, pyridine, and combinations thereof.

The present invention additionally provides methods of providing UV radiation protection to a subject. Such a method can include disposing a composition including a plurality of nanodiamond particles dispersed in a cosmetically acceptable carrier onto a subject's skin, wherein the nanodiamond particles include at least one sun-block functional group operable to provide ultraviolet radiation protection to the skin. One specific aspect further includes evaporating the carrier to leave the nanodiamond particles as a residue on the subject's skin.

There has thus been outlined, rather broadly, various features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

DETAILED DESCRIPTION OF THE INVENTION

Definitions

In describing and claiming the present invention, the following terminology will be used in accordance with the definitions set forth below.

The singular forms "a," "an," and "the" include plural referents unless the context clearly dictates otherwise. Thus, for example, reference to "a solvent" includes reference to one or more of such solvents, and reference to "the dispersant" includes reference to one or more of such dispersants.

As used herein, "subject" refers to a mammal that may benefit from the administration of a composition or method of this invention. Examples of subjects include humans, and may also include other animals such as horses, pigs, cattle, dogs, cats, rabbits, and the like, including aquatic mammals.

As used herein, "formulation" and "composition" may be used interchangeably and refer to a combination of elements that is presented together for a given purpose. Such terms are well known to those of ordinary skill in the art.

As used herein, "carrier" and "acceptable carrier" can be used interchangeably and refer to a carrier that may be combined with a plurality of nanodiamond particles in order to provide a desired composition. Those of ordinary skill in the art will recognize a number of carriers that are well known for making specific compositions for administration to tissue.

As used herein, "cosmetically acceptable carrier" refers to a material that is suitable for application to generally external tissue, including skin and keratinous surfaces or other areas of the body. Upon application, cosmetically acceptable carriers are substantially free of adverse reactions with skin and other tissue.

As used herein, the term "cosmeceutical" refers to cosmetic products that impart medicinal or health benefits, as with nutraceuticals. Typically, cosmeceuticals are applied to the skin.

As used herein, the term "topical," in reference to administration, means applying an active ingredient directly to the skin surface. The active ingredient may be in the form of a composition, to aid in application. Examples of topical formulations include but are not limited to lotions, ointments, creams, gels, sprays, pastes, and powders.

"Skin," "skin surface," "derma," "epidermis," and similar terms are used interchangeably herein, and refer to not only the outer skin of a subject comprising the epidermis, but also to mucosal surfaces to which a composition may be administered. Examples of mucosal surfaces include the mucosal of the respiratory (including nasal and pulmonary), oral (mouth and buccal), vaginal, introital, labial, and rectal surfaces.

As used herein, "nanoparticle" refers to a nano-sized particle comprising substantially carbon and/or boron nitride. In one aspect, the nanoparticles may be diamond.

As used herein, "remedial" is an adjective referring to remedying, correcting, treating, improving, or preventing an undesirable condition. A remedial composition can therefore be formulated to remove undesirable materials such as sebum, dead skin, and the like from the skin. Similarly, remedial compositions can be configured to remove, prevent or minimize formation of undesirable elements such as odor-producing bacteria and the like.

As used herein, "bonded" and "bonding," when used in connection with nanodiamond contact with biological materials, refers to bonding such as covalent bonding, ionic bonding, mechanical bonding, van der Waals attractions, hydrogen bonding, or other intermolecular attractive forces.

"Effective amount" refers to an amount of a substance which is sufficient to achieve its intended purpose or effect. Various biological factors may affect the ability of a delivered substance, such as nanodiamond particles, to perform its intended task. Therefore, an "effective amount" may be dependent on such biological factors.

As used herein, "functionalized nanodiamonds" are those nanodiamond particles having surfaces with attached functional groups. The functional groups can absorb or reflect UV radiation, and can be bonded to the nanodiamond particles with a variety of covalent linkages and non-covalent bonding mechanisms. A non-limiting list of covalent linkages includes amines, olefins, thiols, disulfides, and the like. Also, functional groups can be covalently bonded to dangling electrons on the nanodiamond surface. Thus the purposeful attachment and surface functionalization of nanodiamond particles can include any known means for functionalizing a diamond surface. Potential methods are discussed in U.S. application Ser. No. 11/897,010, filed Aug. 27, 2007, which is incorporated herein by reference.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The Invention

The present invention provides compositions containing nanodiamond particles and associated methods. More specifically, nanodiamond particles can be included in remedial and cosmetic compositions to provide a number of advantages. Additional information regarding nanodiamond compositions can be found in U.S. Pat. No. 7,294,340, filed on Mar. 30, 2004, and in U.S. application Ser. No. 11/640,136, filed on Dec. 14, 2006, both of which are incorporated herein by reference.

The presence of nanodiamond particles can enhance mechanical properties, provide improved bonding of certain biological materials, and protect a subject from ultraviolet (UV) radiation. Nanodiamond particles can also reduce and prevent the formation of free radicals. Free radical theory teaches that free radicals may be responsible for aging through causing damage to protein, lipid, and nucleic acids. Over time, the damage caused by free radicals leads to reduction of function, which dominoes into greater problems throughout the cell, organ, and body. Free radicals have also been linked to disease. Present theories link such diseases as cancer, diabetes, Alzheimer's disease, arthritis, and atherosclerosis to free radical damage. Visible signs of aging, such as wrinkles, have also been linked to free radical damage. Fortunately, it was recently discovered that nanodiamonds can prevent or limit such free radical formation. By supplying nanodiamond particles to tissue, then, the nanodiamonds act to prevent disease and perhaps aging.

In one aspect, a remedial healthcare nanodiamond composition includes a cosmetically acceptable carrier and a plurality of nanodiamond particles dispersed in the carrier with a dispersant, where the nanodiamond particles have an average size of from about 0.5 nm to about 50 nm. The composition can also include a sun-block agent.

In another aspect, a sunscreen composition is provided. Such a composition includes a cosmetically acceptable carrier and a plurality of nanoparticles dispersed in the carrier with a dispersant. While the some nanoparticles such as nanodiamond particles themselves can impart sun-block protection, in some aspects the nanoparticles can include at least one sun-block functional group operable to provide ultraviolet radiation protection. Non-limiting examples of nanoparticles can include nanodiamond, nanographite (or nanographene), nanohexagonal boron nitride, nanocubic boron nitride, and the like. It should be noted that the term "nanodiamond" is used throughout much of the specification for convenience. Thus the discussions of "nanodiamond" should also be applied to nanoparticles in general where applicable.

In yet another aspect, a method of providing ultraviolet radiation protection to a subject is provided. Such a method includes disposing a composition including a plurality of nanodiamond particles dispersed in a cosmetically acceptable carrier onto a subject's skin. In one specific aspect, the nanodiamond particles include at least one sun-block functional group operable to provide ultraviolet radiation protection to the skin.

As has been described, UV protection can be achieved through the application of the present compositions to the skin. Various compositions are contemplated, including liquid emulsions, cream emulsions, powders, dispersions, creams, gels, suspensions, sticks, lotions, water-based dispersions, and the like. Lotions can include skin lotions, facial lotions, moisturizers, liquid foundations, eye creams, facial masks (even those which are designed to dry while on the skin), cover up, sunscreens, moisturizers, or any formulation with the consistency matching those products listed. The nanodiamonds could be included in a cosmetic, thus creating a cosmeceutical. Non-limiting examples of cosmetics include lipstick, lip gloss, lip liner, liquid foundation, concealer, cream foundation, powder, bronzer, blush (powder, cream, and gel), mascara, eye liner, eye shadow, mineral cosmetics. It naturally follows that the skin may be facial skin, where the nanodiamonds may be administered.

In another aspect, the nanodiamond particles can be dispersed in a volatile or evaporatable carrier, such as a water-based carrier. In such cases, the composition can be applied to the skin and the carrier can be evaporated, leaving a nanodiamond residue that provides UV radiation protection to the subject.

A variety of ingredients are contemplated for inclusion in the present formulations. One of ordinary skill in the art would understand that dispersants, carriers, and other ingredients can vary depending on the specific formulation. Also, carriers can vary according to the desired form of the composition. Generally, however, non-limiting examples of cosmetically acceptable carriers include water, gels, glycerin, alcohols, emollients, fatty acids, fatty alcohols, maltodextrin, carrageenans, MCC, sugars, alcohol sugars, lactose, and combinations thereof.

Nanodiamond particles typically carry an electrical charge, which leads to aggregation and flocculation of particles. In many cases, this aggregation of nanodiamond particles is undesirable. Therefore, an optional dispersant can be included which improves the uniformity of nanodiamond distribution. In this way, a colloidal suspension can be formed in which the nanodiamond particles remain substantially uniformly dispersed over an extended period of time, e.g., typically months or years. Preferably, the nanodiamond particles remain dispersed during the useful shelf-life of the particular composition. The dispersant can be provided in the form of a specific compound separate from the carrier in a liquid nanodiamond composition. However, in certain situations, e.g. for highly viscous compositions, the carrier can also be the dispersant. Thus, in some embodiments such as a solid deodorant, toothpaste, soaps, viscous nail polish, and the like, the carrier can provide sufficient viscous support to prevent agglomeration and/or settling of the nanodiamond particles.

Any suitable dispersant can be used which is compatible with a particular carrier. However, several non-limiting examples of dispersants include anionic surfactants, electrolytes, alcohols, metal chlorides and nitrates of Al, Na, Ca, and Fe, viscous biologically acceptable carriers, and the like. Other suitable nanodiamond dispersants include isopropyl triisosteroyl titanate, polyethylene-oxides, and other anionic surfactants. One specific suitable surfactant which can be used is stearalkonium hectorite. The dispersant can also provide other properties to a composition such as pH control. Further, the amount of dispersant can depend on the amount of nanodiamond present and the viscosity of the composition. However, as a general guideline, the composition can include from 1 wt % to about 30 wt % dispersant.

The compositions of the present invention include a plurality of nanodiamond particles. In one aspect, nanodiamond made by explosive detonation can be used. Such nanodiamond particles contain internal defects, voids, microcracks, and in some cases external radicals such as H, N, O, and the like, that can increase the absorbance of UV radiation by the nanodiamond particles. Sp1 and sp2 bonded carbon associated with the nanodiamond particles can also increase the absorption of UV radiation, thus greatly widening the overall absorption bands of the nanodiamond material.

Various size ranges of nanodiamond particles can be utilized in the present compositions depending on the desired absorption of the composition. Larger nanodiamond particles tend to absorb lower energy radiation. As such, compositions can be formulated to absorb radiation within fairly specific energy ranges by using nanodiamond particles having a size in a specific range. Conversely, compositions can be formulated having a broad range of absorption energies by utilizing a broad range of nanodiamond particle sizes. In one specific aspect, for example, the nanodiamond particles have an average size of from about 0.5 nm to about 50 nm. In another specific example, the nanodiamond particles have an average size from about 0.5 nm to about 10 nm. In yet another specific example, the nanodiamond particles have an average size of less than or equal to about 5 nm. In a further specific example, the nanodiamond particles have an average size from about 50 nm to about 4000 nm. In another aspect, the nanodiamond particles have an average size from about 50 nm to about 2000 nm. In yet another aspect, the nanodiamond particles have an average size from about 50 nm to about 1000 nm. In a further aspect, the nanodiamond particles have an average size from about 100 nm to about 1000 nm. In another aspect, the nanodiamond particles have an average size from about 100 nm to about 500 nm. In yet another aspect, the nanodiamond particles have an average size from about 200 nm to about 500 nm.

Furthermore, the concentration of nanodiamond particles will vary depending on the composition and the desired effect. Because of the effectiveness of the present nanodiamond compositions at absorbing UV radiation, the concentration of nanodiamond particles can be surprisingly low, although such low concentrations are not required. As a practical matter, in one aspect the plurality of nanodiamond particles is from about 1 wt % to about 80 wt % of the composition. In another aspect the plurality of nanodiamond particles is from about 1 wt % to about 60 wt % of the composition. In yet another aspect the nanodiamond particles comprise from about 1 wt % to about 20 wt % of the composition. In a further aspect the nanodiamond particles comprise less than or equal to about 5 wt % of the composition. In another aspect, the concentration of nanodiamond particles in the composition can be less than 200 ppm, or less than 100 ppm, or less than 50 ppm of the total composition.

Nanodiamond particles can be formed using a number of known techniques such as shock wave synthesis, CVD, and the like. In one aspect, the nanodiamond particles can be functionalized. Various functional groups are contemplated, and any functional group capable of providing protection against UV radiation should be considered to be within the present scope. In one aspect, for example, a functional group can include amino, carboxyl, hydroxyl, carbonyl, pyridine, and the like, including combinations thereof. In one specific example, the functional group can be and amino/peptide group. Aromatic, hexa-, and penta-cyclic containing compounds are also contemplated, or in general, any ring structure of carbon or boron nitride that can resonate at UV energies. Thus, such functional groups can be used to absorb UV A, B, and C radiation. In one aspect, the functional group can include benzene, peridine, pyran, thiopyran, and the like. In another aspect, the functional group can include cyclopentane, Pyrrole, furan, thiophene, and the like.

Additionally, nanodiamond materials have a puckered hexagonal structure, so nanodiamond can absorb UV A, B, and C radiation, depending on the size of the nanodiamond and any functionized molecules. Additionally, the nanodiamond particles can be fuctionalized with graphene and/or hexagonal boron nitride to facilitate UV protection. Thus it should be noted that, with or without functionalization of the nanodiamond particles with functional groups, UV radiation protection can be provided through the application of such particles to the skin.

In addition to providing UV radiation protection, introduction of nanodiamond particles into a composition can provide a number of beneficial properties. One of such beneficial properties is an ability of nanodiamonds to absorb oil and other organic materials. Carbon atoms are very small (about 1.5 angstroms); thus, various forms of carbon can pack to form a high atomic concentration. Accordingly, diamond has the highest atomic concentration (176 atom/nm$^3$) of all known materials. This high atomic concentration contributes to the exceptional hardness of diamond. As a result, any given surface area of a nanodiamond particle can include many more atoms than other nanoparticles of the same size.

Although diamond is highly stable, if the nanodiamond surface is free of adsorbent or absorbent, i.e. clean, it is thought that carbon atoms on the surface contain unpaired electrons that are highly reactive. As a result, nanodiamond particles can readily bond to and effectively absorb a variety of atomic species. For example, small atoms such as H, B, C, N, O, and F can be readily adsorbed on the nanodiamond surface, although other atoms can also be absorbed. Hence, nanodiamond particles, with their vast number of surface atoms, can hold a large amount of such adsorbed atoms. For example, nanodiamond particles are capable of absorbing almost as many hydrogen atoms as the number of exposed carbon atoms present on the surface of the nanodiamond material. Thus, nanodiamond particles can be used as storage sites for hydrogen. In addition, those small atoms are building blocks, e.g., H, CO, OH, COOH, N, CN and NO, of organic materials including biological molecules. Consequently, nanodiamond particles can readily attach to amino acids, proteins, cells, DNA, RNA, and other biological materials, and nanodiamond particles can be used to remove skin oils, facial oils, compounds that result in body odor, bacteria, etc.

As has been described, in one aspect the compositions of the present invention can be formulated as a lotion. The lotion can include an acceptable carrier and a plurality of nanodiamond particles. Acceptable carriers are known in the art and can include, for example, glycerin, alcohols, water, gels, combinations of these materials, and other known carriers. In addition, the lotion can include additives such as fragrance, colorants, vitamin E, herbal supplements, antibiotics, UV absorbers, sun-block agents, and the like. Specific examples of sun-block agents can include $TiO_2$, $CEO_2$, ZnO, and combinations thereof. A more detailed description of various lotions can be found in U.S. Pat. Nos. 6,207,175 and 6,248,339, which are each incorporated herein by reference in their respective entireties.

The present compositions can also be formulated so as to be applied with a tissue or wipe. The tissue or wipe lotion can include an acceptable carrier and a plurality of nanodiamond particles. Acceptable carriers are known in the art and can include, for example, glycerin, alcohols, water, gels, combinations of these materials, and other known carriers. In addition, the lotion can include additives such as fragrance, colorants, vitamin E, herbal supplements, antibiotics, UV absorbers, sun-block agents, and the like. A more detailed description of facial lotion formulations can be found in U.S. Pat. No. 6,428,794, which is incorporated herein by reference in its entirety. The wipe can thus be used to conveniently apply a sunscreen composition to a subject.

It is to be understood that the above-described compositions and methods are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in materials, temperature, function, order, and manner of operation, assembly and use may be made without departing from the principles and concepts set forth herein.

What is claimed is:

1. A remedial healthcare nanodiamond composition, comprising:
    a cosmetically acceptable carrier;
    a plurality of nanodiamond particles dispersed in the carrier with a dispersant, the nanodiamond particles having an average size of from about 0.5 nm to about 50 nm; and
    a sun-block agent.

2. The composition of claim 1, wherein the composition is formulated as a lotion.

3. The composition of claim 2, wherein the dispersant is a member selected from the group consisting of anionic surfactants, electrolytes, alcohols, metal chlorides, metal nitrates, viscous biologically acceptable carriers, and mixtures thereof.

4. The composition of claim 1, wherein the plurality of nanodiamond particles comprise from about 1 wt % to about 60 wt % of the composition.

5. The composition of claim 1, wherein the plurality of nanodiamond particles have an average size from about 0.5 nm to about 10 nm.

6. The composition of claim 1, wherein the cosmetically acceptable carrier is a member selected from the group consisting of water, gels, glycerin, alcohols, emollients, fatty acids, fatty alcohols, maltodextrin, carrageenans, MCC, sugars, alcohol sugars, lactose, and combinations thereof.

7. The composition of claim 1, wherein the sun-block agent is a member selected from the group consisting of amino, carboxyl, hydroxyl, carbonyl, pyridine, $TiO_2$, $CEO_2$, $ZnO$, and combinations thereof.

8. The composition of claim 7, wherein the sun-block agent is coupled to the nanodiamond particles.

* * * * *